United States Patent
Chambers

[11] Patent Number: 6,129,759
[45] Date of Patent: *Oct. 10, 2000

[54] FROSTED HAPTIC INTRAOCULAR LENS

[75] Inventor: Thomas J. Chambers, Upland, Calif.

[73] Assignee: STAAR Surgical Company, Inc., Monrovia, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/988,185

[22] Filed: Dec. 10, 1997

[51] Int. Cl.[7] ........................................................ A61F 2/16
[52] U.S. Cl. .......................................... 623/6.17; 623/6.11
[58] Field of Search .............................. 623/6, 6.11, 6.17

[56] References Cited

U.S. PATENT DOCUMENTS

| | | | |
|---|---|---|---|
| 4,449,257 | 5/1984 | Koeniger | 3/13 |
| 4,605,409 | 8/1986 | Kelman | 623/6 |
| 4,676,791 | 6/1987 | LeMaster et al. | 623/6 |
| 4,687,485 | 8/1987 | Lim et al. | 623/6 |
| 4,704,123 | 11/1987 | Smith | 623/6 |
| 4,808,181 | 2/1989 | Kelman | 623/6 |
| 4,846,832 | 7/1989 | Wichterle | 623/6 |
| 4,865,601 | 9/1989 | Caldwell et al. | 623/5 |
| 4,932,968 | 6/1990 | Caldwell et al. | 623/6 |
| 5,011,494 | 4/1991 | von Recum et al. | 623/11 |
| 5,074,942 | 12/1991 | Kearns et al. | 623/6 X |
| 5,405,385 | 4/1995 | Heimke et al. | 623/6 |
| 5,507,805 | 4/1996 | Koeniger | 623/6 |
| 5,578,080 | 11/1996 | McDonald | 623/6 |

Primary Examiner—Dinh X. Nguyen

[57] ABSTRACT

A deformable intraocular lens having frosted and/or colored haptic portions. The frosted haptic portions increase the frictional resistance to movement or rotation within the inner structure of the eye once implanted.

23 Claims, 4 Drawing Sheets

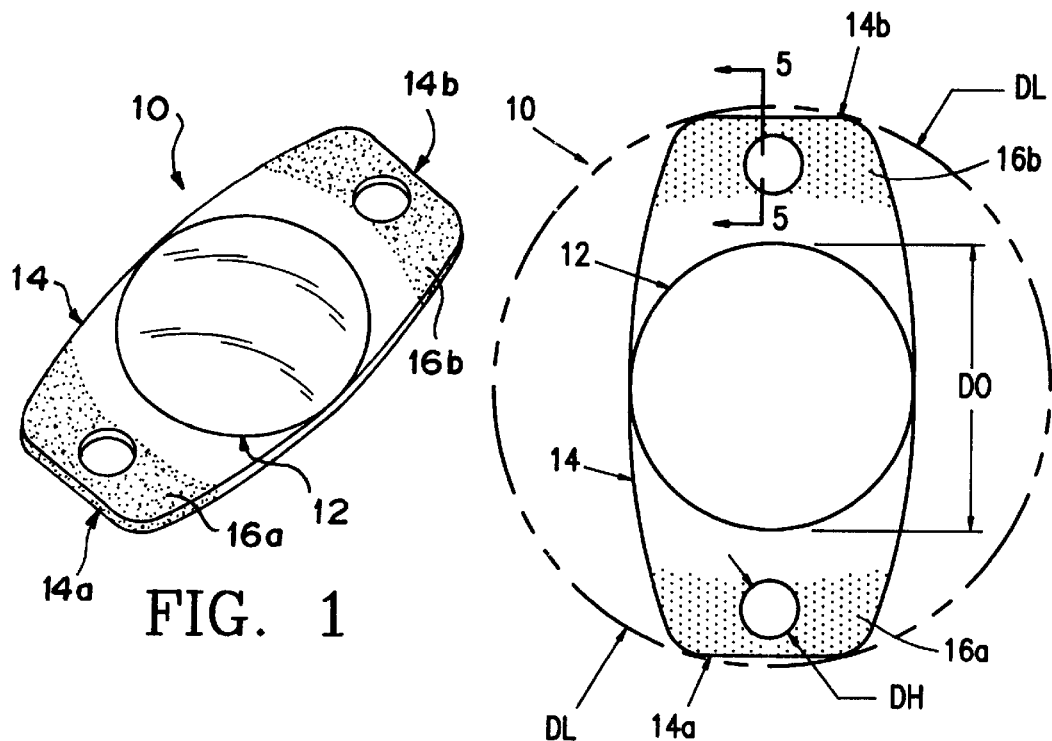
FIG. 1
FIG. 2
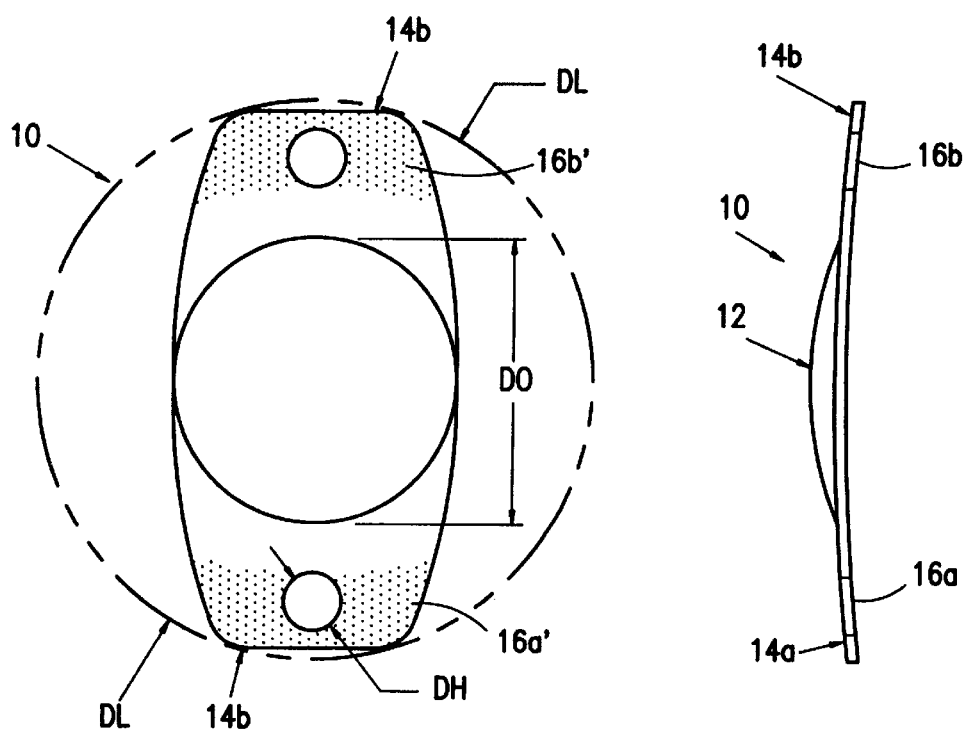
FIG. 3
FIG. 4

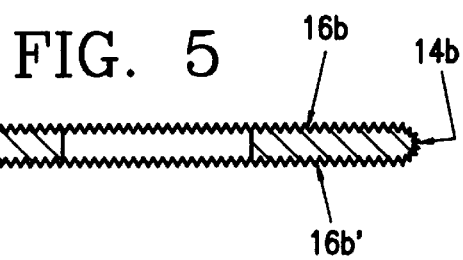
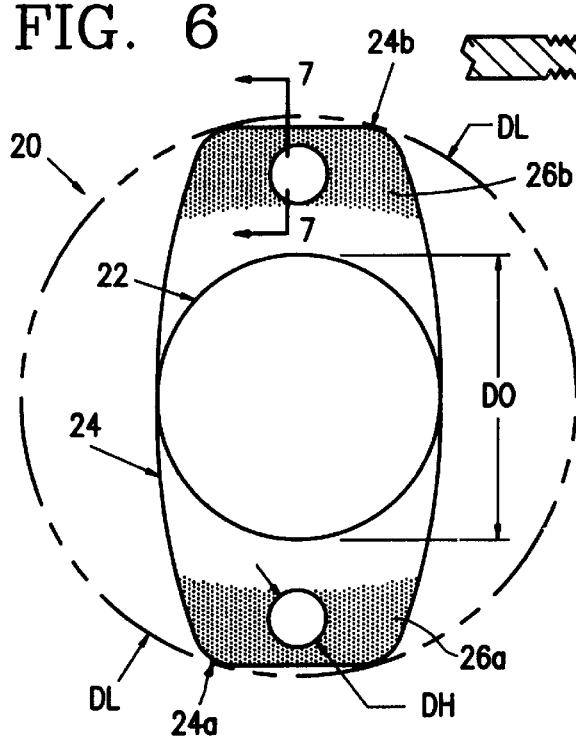
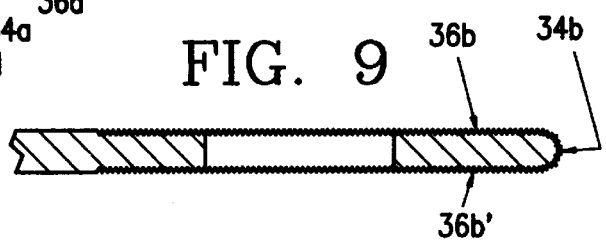
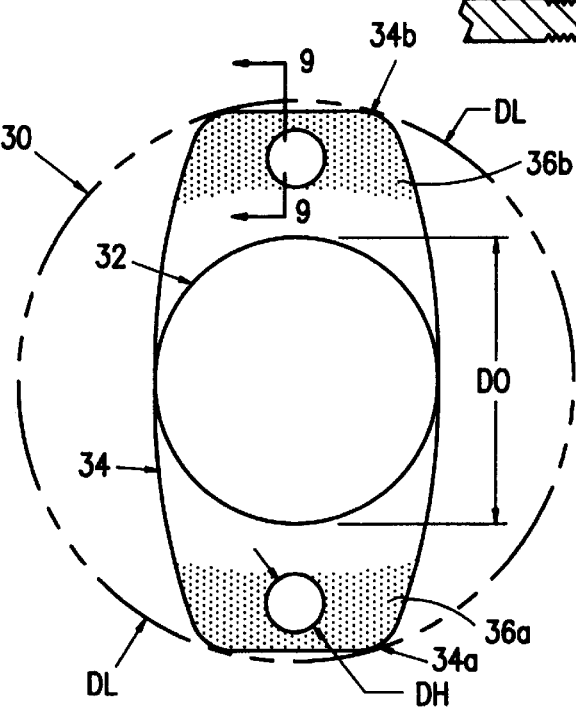

FROSTED HAPTIC INTRAOCULAR LENS

FIELD OF THE INVENTION

The present invention is directed to an intraocular lens having frosted haptic portions. The present invention is particularly suitable for one-piece plate-type intraocular lenses.

BACKGROUND OF THE INVENTION

The concept of a deformable intraocular lens (IOL) was invented and developed in the early 1980's by Dr. Mazzacco who became a founder of Staar Surgical Company of Monrovia, Calif. Staar Surgical Company has been an innovator of deformable IOLs, and is a leading manufacturer and marketer of deformable IOLs in the United States and throughout the world.

There exists two main types of deformable intraocular lenses having different types of configurations for attaching the lens in the eye. Specifically, there exists a three (3) piece lens, including a lens portion and two separate loop-type haptics each having one end embedded in the lens portion of the lens. The other main type is a plate-type intraocular lens having a pair of opposed haptics extending from the lens portion and molded together as a one-piece integral construction.

Further, intraocular lenses can be differentiated by cataract lens replacement-type in which the natural crystalline lens is removed and replaced by an intraocular lens, and a refractive type of intraocular lens to be added in front of the natural crystalline lens without removal thereof.

Currently, the haptic portions of both three (3) piece type IOLs and one-piece plate-type IOLs have substantially smooth surface textures due to the various methods of manufacturing these types of lenses. In particular, plate-type intraocular lenses are tumble polished so that the entire surface is very smooth and highly transparent.

Further, one-piece plate-type IOLs currently being marketed and sold are uniformly optically clear and have no appreciable coloration. Specifically, currently marketed one-piece plate-type IOLs are made from virgin silicon or acrylic based materials that are optically clear and not colored before and after molding thereof. Any appreciable coloring (e.g. clouding or browning) of this material is considered defective, and such lenses are typically discarded under quality control.

SUMMARY OF THE INVENTION

An object of the present invention is to provide an improved deformable intraocular lens.

A second object according to the present invention is to provide a deformable intraocular lens having one or more frosted and/or textured surface portions.

A third object according to the present invention is to provide a deformable intraocular lens having haptic portions having one or more frosted and/or textured surface portions.

A fourth object of the present invention is to provide a three (3) piece type intraocular lens having haptic portions with one or more textured surface portions.

A fifth object of the present invention is to provide a one-piece plate-type intraocular lens having plate-type haptics with one or more frosted and/or textured surface portions.

A sixth object of the present invention is to provide a deformable one-piece plate-type deformable intraocular lens having plate-type haptics with frosted and/or textured surface end portions.

The present invention is directed to various types of deformable intraocular lenses having frosted and/or textured haptic portions. These surface finishes alter the optical and physical characteristics (e.g. optical clarity, surface friction, surface adhesion, surface tension, porosity, surface hardness, etc.) of the surfaces of the haptic portions of the deformable IOLs. For example, the haptic portions can be provided with a frosted finish that effects the transmission of light through the haptic portions, the haptic portions can be provided with a matte finish that scatters reflected light in all directions; and/or the haptic portions can be provided with an etched finish that provides a roughened surface texture finish to increase frictional contact with the inner eye tissue.

The present invention encompasses all types of deformable intraocular lenses, however, one-piece plate-type deformable intraocular lenses are of particular interest with respect to the present invention. The deformable intraocular lenses include three (3) piece type IOLs, one-piece plate-type intraocular IOLs, deformable refractive correction IOLs (e.g. Staar Surgical Company's Intraocular Contact Lens) and other types of anterior chamber and/or posterior chamber type IOLs. Further, the present invention is directed to providing one-piece plate-type IOLs with colored haptic portions. Specifically, limited portions or the entire haptics portions of one-piece plate-type IOLs are colored.

The deformable IOLs according to the present invention are provided with haptic portions that include frosted and/or textured surfaces. Specifically, portions of the surfaces or the entire surfaces of the haptic portions are frosted and/or textured. The frosted surface portions can be continuous or non-continuous with other portions. Various designs of the frosted surface portions, for example, can include stripes, checkerboard, dots, circles, triangles, squares, pentagons, octagons, lattice or virtually any other type of design including potentially art work. The frosting can be provided on the front, back and/or edge surfaces.

The frosted and/or textured surface portions can be applied to the deformable IOLs by various methods including molding or surface texturing. Specifically, surfaces of the mold can be frosted or textured (e.g. sandblasting, electrode discharge machining (EDM), shot peening, laser etching chemical etching, sputtering, vapor depositing, etc.). Alternatively or in addition, the surfaces of the haptic portions of the deformable IOLs can be frosted or textured by, for example, sandblasting or shot peening haptic portion of the lens, chemically etching frosted surface portions, irradiating portions to become frosted or non-frosted, chemically etching portions to become frosted or non-frosted, masking techniques, irradiating, surface modifying or other various techniques to make portions of the haptic transparent, lightly frosted or textured, medium frosted or textured, highly frosted or textured, or frosted or textured to any degree therebetween.

The frosted and/or textured surface portions of the haptic portions increase friction in the interface between tissue and haptic portion to increase the extent of anchoring the IOL within the eye. It is highly desirable to anchor and minimize movement of the IOL and prevent any relevant movement (e.g. rotation) between the IOL and inner structure of the eye. Typically, there only exists the possibility of some movement, post operatively prior to healing of the tissue in the eye (i.e. up to several weeks). It is during this time period that it would be highly desirable to prevent any relative movement and/or rotation of the implanted IOL within the eye structure.

Based on mechanics, it is highly desirable that tip portions of the haptic portions are frosted and/or textured to provide the greatest moment arm for frictional forces applied from the eye tissue on the haptic portions to prevent relative movement and/or rotation of the IOL within the eye structure. Further, both sides and the edges of the haptics portions are preferably frosted and/or textured to increase the total surface area that is frosted, and thus increase the amount of frictional resistance to movement of the IOL within the eye structure.

The frosted and/or textured surfaces of the haptic portions will also decrease the amount of light being transmitted through the haptic portions.

In the context of a one-piece plate-type IOL according to the present invention, a portion of one or both haptic portions can be intentionally colored. The coloration can render the haptics opaque, or partially transmissive (i.e. translucent). The coloration can be used independent of any surface frosting, or in combination therewith. For example, the same surface portions can be both frosted and colored, or different portions can be frosted and not colored while other portions are not frosted, but colored.

The coloration can be utilized to reduce the transmittance of light through the haptic portions, for marking the lens (e.g. trademark logos, lens orientation markings, art work, bar codes, etc.).

BRIEF DESCRIPTION OF THE DRAWINGS

FIG. 1 is a perspective view of an intraocular lens according to the present invention having frosted surfaces on the haptic portions.

FIG. 2 is a top planar view of the intraocular lens shown in FIG. 1.

FIG. 3 is a rear view of the deformable intraocular lens show in FIG. 1.

FIG. 4 is a side elevational view of the deformable intraocular lens show in FIG. 1.

FIG. 5 is a partial broken-away transverse cross-sectional view of a haptic portion, as indicated in FIG. 2.

FIG. 6 is a top planar view of another embodiment of the deformable intraocular lens according to the present invention having colored zones on the haptic portions.

FIG. 7 is a partial broken-away side cross-sectional view of the haptic portion, as indicated in FIG. 6.

FIG. 8 is a front elevational view of an intraocular lens according to the present invention having both frosted and colored haptic portions.

FIG. 9 is a partial broken-away side cross-sectional view of the haptic portion, as indicated in FIG. 8.

DETAILED DESCRIPTION OF PREFERRED EMBODIMENTS

Definitions

Figure 10:
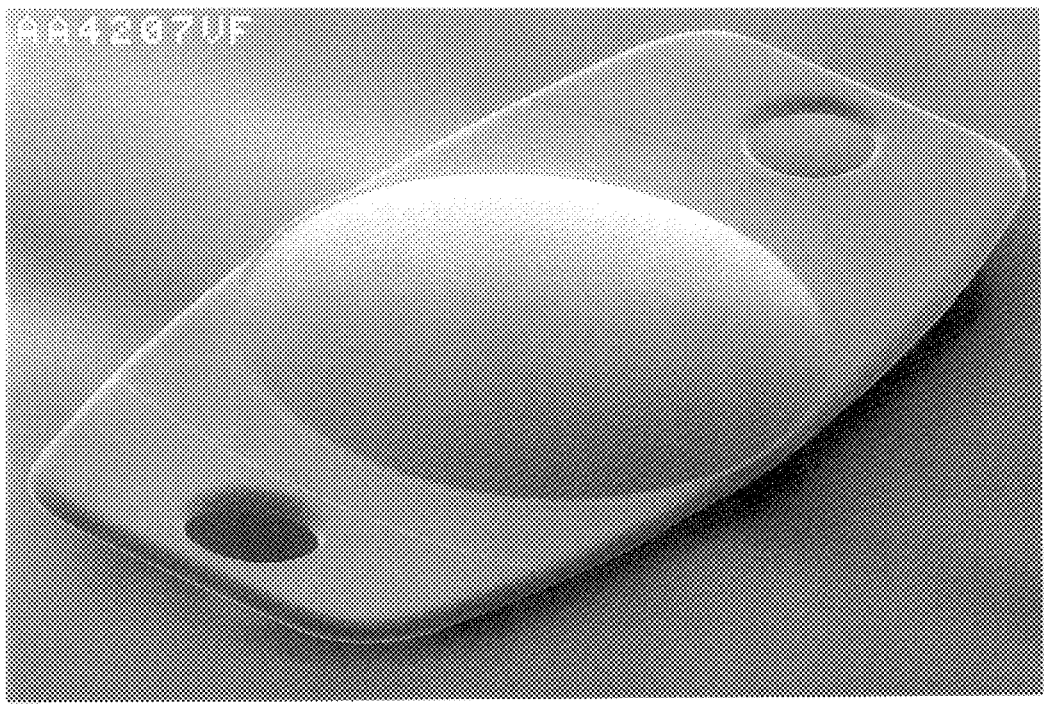
FIG. 10 is a perspective view of an actual one-piece plate-type deformable intraocular lens according to the present invention by electron micrograph showing details of the frosted haptic portions.

Deformable intraocular lens—means an intraocular lens made of an elastic material capable of being folded, rolled or compressed to fit through a relatively small incision (e.g. 2.5 to 3.0 mm) made in the eye. For example, typical deformable intraocular lens are made of silicone elastomer, acrylic elastomer, or collagen-based polymer (e.g. COLLAMER made by STAAR Surgical of Monrovia, Calif.).

Flaws—mean unintentional, unexpected, and unwanted interruptions.

Frosted Surface—means a roughened surface that reduces the transmission of light therethrough.

Lay—means the direction of the predominant surface pattern, ordinarily determined by the production method used.

Matte Surface—means a dull surface that scatters reflected light in all directions.

Measured profile—means a representation of the profiled obtained by instrumental or other means.

Measured surface—means a representation of the surface obtained by instrumental or other means.

Nominal profile—means a profile of the nominal surface; it is the intended profile (exclusive of any intended roughness profile).

Nominal surface—means the intended surface contour (exclusive of any intended surface roughness), the shape and extent of which is usually shown and dimensioned on a drawing or descriptive specification.

Peak—means the point of maximum height on that portion of a profile that lies above the centerline and between two intersections of the profile with the centerline.

Roughness—means the finer irregularities of surface texture, usually including those irregularities which result from the inherent action of the production process. These are considered to include traverse feed marks and other irregularities within the limits of the roughness sampling length.

Roughness sampling length—means the sampling length within which the roughness average is determined. This length is chosen, or specified, to separate the profile irregularities which are designated as roughness from those irregularities designated as waviness.

Roughness spacing—means the average spacing between adjacent peaks of the measured profile within the roughness sampling length.

Sampling length—means the nominal spacing within which a surface characteristic is determined.

Spacing—means the distance between specified points on the profile measured parallel to the nominal profile.

Surface texture—means the repetitive of random deviations from the nominal surface which form the three-dimensional topography of the surface. Surface texture includes roughness, waviness, lay and flaws.

Valley—means the point of maximum depth on that portion of a profile that lies below the centerline and between two intersections of the profile with the centerline.

Waviness—means the more widely spaced component of surface texture. Unless otherwise noted, waviness is to include all irregularities whose spacing is greater than the roughness sampling length and less than the waviness sampling length. Waviness may result from such factors as machine or work deflections, vibration, chatter, heat-treatment or warping strains. Roughness may be considered as being superposed on a 'wavy' surface.

Waviness spacing—means the average spacing between adjacent peaks of the measured profile within the waviness sampling length.

These definitions are based on American National Standard ANSI B46.1-1985.

Frosted Haptic Portions

A plate-type deformable intraocular lens 10 according to the present invention is shown in FIG. 1. The deformable intraocular lens 10 comprises a lens portion 12 and haptic portion 14 including haptic portions 14a and 14b. The haptic portions 14a and 14b are provided with frosted surface portions 16a and 16b, respectively. As shown in FIGS. 2 and 3, both sides of the haptic portions 14a and 14b are provided with frosted surface portions 16a and 16b, respectively.

Colored Haptic Portions

Another embodiment of a deformable intraocular lens 20 according to the present invention is shown in FIG. 6. The intraocular lens 20 includes a lens portion 22 and haptic portion 24, including haptic portions 24a and 24b. The haptic portions 24a and 24b are provided with colored or tinted portions 26a and 26b, respectively.

The colored portions 24a and 24b can be made by coloring, dying, painting, masking, coating, tinting or other suitable process of applying a coloring material to the interior and/or surface of the haptic portion. The coloring material can be added to the lens material (e.g. before or during formation of the lens), or used to treat the lens material (e.g. dying surface, coating surface, modifying surface or interior with radiation after formation of the lens). The coloring material can be of a type to leave the haptic material transparent with coloring (e.g. tinting), or can be of a type to make the haptic material opaque (e.g. color pigment or dye).

A further embodiment of a deformable intraocular lens 30 according to the present invention is shown in FIG. 8. The intraocular lens 30 includes a lens portion 32 and haptic portion 34, including haptic portions 34a and 34b. The haptic portions 34a and 34b are provided with both frosted and colored (or tinted) portions 36a and 36b, respectively. The term DH refers to the diameter of the holes through the haptic portions 34a and 34b and the term DL refers to the diameter of the lens 30.

Surface Frosting and/or Texturing

The frosted and/or textured surface portions of the haptics are provided by forming or making portions of the haptic having a particular surface roughness. Specifically, the roughness of a surface is based on the dimensional aspects of gaps and protrusions in the surface of the haptics. The surface roughness can be further characterized by the mean value of the width of the gaps, the mean value of the thickness of the protrusions, the mean value of the depth of the gaps, and the mean value of the spacing between the gaps. This manner of characterizing surface roughness in the context of an intraocular lens is set forth in U.S. Pat. No. 5,405,385 to Heimke et al. U.S. Pat. No. 5,405,385 is fully incorporated by reference herein.

The desired extent of frosting of the frosted surface portions of the haptic portions in the IOLs according to the present invention is to preferably provide a mean value of the width of the gaps of from 8–128 microns, a mean value of thickness of the protrusions of from 8–128 microns, a mean value of the depth of the gaps of 8–128 microns, and a mean value of spacing between gaps in a range of 8–128 microns. These parameters will be referred to in general as the mean surface roughness. The mean surfaces roughness is the average of the mean values of width of the gaps, mean value of thickness of the protrusions, and mean value of the depth of the gaps. More preferably, the mean value of width of the gaps is from 16–64 microns, the mean value of the thickness of the protrusions is from 16–64 microns, the mean value of the depth of the gaps is 16–64 microns, and the mean value of the spacing between gaps is 16–64 microns. The most preferred surface roughness is characterized by a mean value of width of the gaps of 32 microns, a mean value of the thickness of the protrusions of 32 microns, the mean value of the depths of the gaps of 32 microns, and the mean value of the spacing between the gaps of 32 microns.

EXAMPLE

Figure 11:
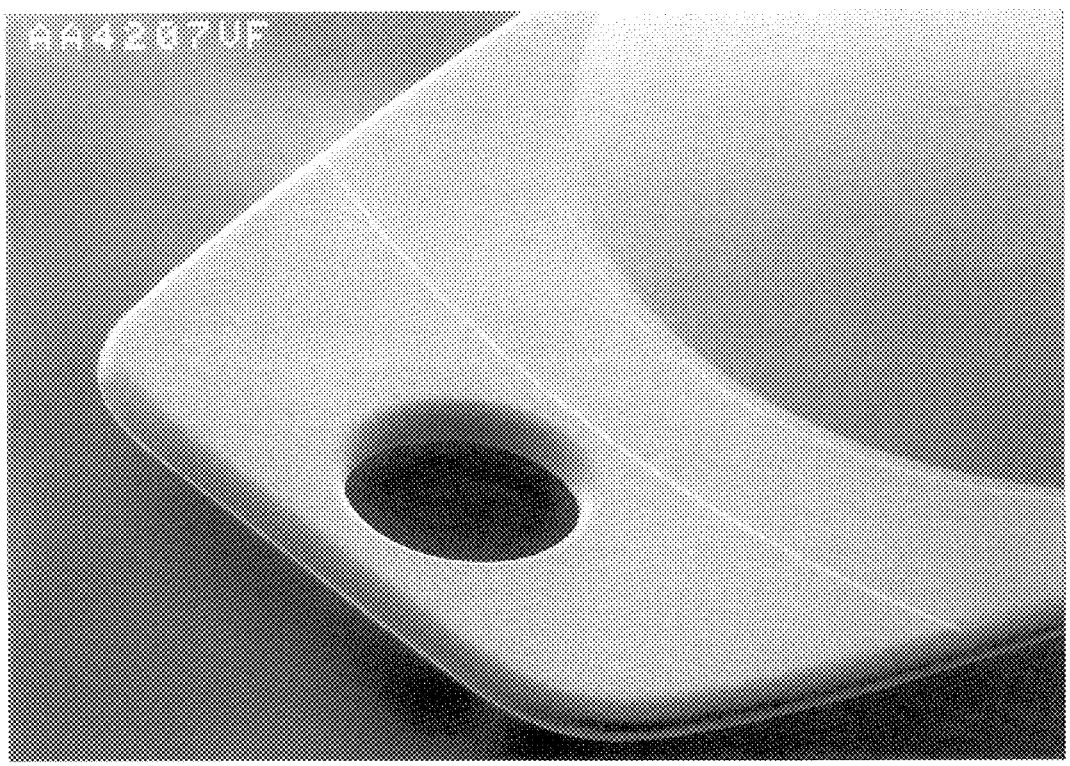
FIG. 11 is a detailed partial broken-away perspective view of the IOL shown in FIG. 10.

A one-piece plate-type deformable intraocular lens according to the present invention was made by the following technique, and is shown in FIGS. 10 and 11. The deformable IOL shown in FIG. 10 was made by injection molding standard silicon polymer material in a metal mold, followed by tumble polishing.

The metal mold was prepared by electro discharge machining (EDM) to cut the mold cavity. The lens portion and inner portions of the haptics were then highly polished to finalize the mold while the portions to mold the frosted haptic portions were left roughened. The lens was then molded by conventional molding techniques for manufacturing the silicon deformable intraocular lens.

What is claimed is:

1. A plate-type deformable intraocular lens, comprising:

a lens portion; and a pair of oppositely disposed plate-type haptic portions, said haptic portions including a frosted surface portion configured to reduce the transmission of light therethrough, said frosted portion having a mean surface roughness in the range of 16 to 64 microns.

2. A lens according to claim 1, wherein one side of said haptic portions is frosted.

3. A lens according to claim 1, wherein both sides of said haptic portions are frosted.

4. A lens according to claim 1, wherein an entire surface of said haptic portions is frosted.

5. A lens according to claim 1, wherein a portion less than an entire surface of said haptic portions is frosted.

6. A lens according to claim 1, wherein said mean surface roughness is most preferably about 32 microns.

7. A lens according to claim 1, wherein at least a portion of said haptic portions is colored.

8. A lens according to claim 1, wherein at least a portion of said haptic portions is translucent.

9. A lens according to claim 1, wherein at least a portions of said haptic is opaque.

10. A lens according to claim 7, wherein at least a portions of said haptic is opaque.

11. A lens according to claim 8, wherein at least a portions of said haptic is opaque.

12. A deformable intraocular lens, comprising:

a lens portion; and a haptic portion, said haptic portion including a frosted portion configured to reduce the transmission of light therethrough wherein said frosted portion is defined by a mean surface roughness in the range of 8 to 128 microns.

13. A lens according to claim 12, wherein one side of said haptic portion is frosted.

14. A lens according to claim 12, wherein both sides of said haptic portion are frosted.

15. A lens according to claim 12, wherein an entire surface of said haptic portion is frosted.

16. A lens according to claim 12, wherein a portion less than an entire surface of said haptic portion is frosted.

17. A lens according to claim 12, wherein said mean surface roughness is defined by a mean surface roughness in the range of 16 to 64 microns.

18. A lens according to claim 17, wherein said mean surface roughness is about 32 microns.

19. A lens according to claim 12, wherein at least a portion of said haptic portion is colored.

20. A lens according to claim 12, wherein at least a portion of said haptic portion is translucent.

21. A lens according to claim 12, wherein at least a portion of said haptic is opaque.

22. A lens according to claim 19, wherein at least a portion of said haptic is opaque.

23. A lens according to claim 20, wherein at least a portion of said haptic is opaque.

\* \* \* \* \*